US007622497B2

(12) United States Patent
Cai et al.

(10) Patent No.: US 7,622,497 B2
(45) Date of Patent: Nov. 24, 2009

(54) DERIVATIVES OF GAMBOGIC ACID AND ANALOGS AS ACTIVATORS OF CASPASES AND INDUCERS OF APOPTOSIS

(75) Inventors: Sui Xiong Cai, San Diego, CA (US); Songchun Jiang, San Diego, CA (US); Han-Zhong Zhang, San Diego, CA (US)

(73) Assignee: Cytovia, Inc., Tarrytown, NY (US)

( * ) Notice: Subject to any disclaimer, the term of this patent is extended or adjusted under 35 U.S.C. 154(b) by 623 days.

(21) Appl. No.: 10/580,263

(22) PCT Filed: Dec. 17, 2004

(86) PCT No.: PCT/US2004/042292

§ 371 (c)(1),
(2), (4) Date: May 25, 2006

(87) PCT Pub. No.: WO2005/060663

PCT Pub. Date: Jul. 7, 2005

(65) Prior Publication Data

US 2007/0093456 A1 Apr. 26, 2007

Related U.S. Application Data

(60) Provisional application No. 60/530,256, filed on Dec. 18, 2003.

(51) Int. Cl.
  *A61K 31/5377* (2006.01)
  *A61K 31/496* (2006.01)
  *A61K 31/352* (2006.01)
  *C07D 265/30* (2006.01)
  *C07D 493/22* (2006.01)
  *C07D 241/04* (2006.01)

(52) U.S. Cl. .................. 514/450; 544/109; 544/357; 514/232.5; 514/252.11; 514/316; 514/338; 514/393; 546/187; 546/190; 548/303.1; 549/268

(58) Field of Classification Search ............... 549/268; 514/450, 232.5, 252.11, 316, 338, 393; 544/109, 544/357; 546/187, 190; 548/303.1, 326
See application file for complete search history.

(56) References Cited

U.S. PATENT DOCUMENTS

| 3,989,816 | A | 11/1976 | Rajadhyaksha | |
|---|---|---|---|---|
| 4,444,762 | A | 4/1984 | Rajadhyaksha | |
| 6,335,429 | B1 | 1/2002 | Cai et al. | |
| 6,462,041 | B1 * | 10/2002 | Cai et al. | 514/232.5 |
| 6,613,762 | B2 | 9/2003 | Cai et al. | |
| 7,176,234 | B2 | 2/2007 | Cai et al. | |

FOREIGN PATENT DOCUMENTS

WO  WO 00/44216 A2  8/2000
WO  WO 2004/002428 A2  1/2004

OTHER PUBLICATIONS

Adawadkar, P.D. et al., "Colouring Matters of *Garcinia morella*: Part VIII—Morellinol, Dihydromorelloflavone and Morelloflavone-7"-β-glucoside," *Indian J. Chem. 14B*:19-21, Council of Scientific & Industrial Research (1976).

Adjei, A.A. et al., "Synergy of the Protein Farnesyltransferase Inhibitor SCH66336 and Cisplatin in Human Cancer Cell Lines," *Clin. Cancer Res. 7*:1438-1445, American Association for Cancer Research, Inc. (2001).

Ahmad, S.A. et al., "Gamboge. Part II," *J. Chem. Soc.* (C):772-779, The Chemical Society (1966).

Almond, J.B. and Cohen, G.M., "The proteasome: a novel target for cancer chemotherapy," *Leukemia 16*:433-443, Nature Publishing Group (Apr. 2002).

Asano, J. et al., "Cytotoxic Xanthones from *Garcinia hanburyI*," *Phytochem. 41*:815-820, Elsevier Science Ltd. (1996).

Batteux, F. et al., "Gene Therapy of Experimental Autoimmune Thyroiditis by In Vivo Administration of Plasmid DNA Coding for Fas Ligand," *J. Immunol. 162*:603-608, The American Association of Immunologists (1999).

Bhat, H.B. et al., "The Colouring Matters of *Garcinia morella*: Part V—Isolation of Desoxymorellin & Dihydroisomorellin," *Indian J. Chem. 2*:405-410, The Council of Scientific & Industrial Research (1964).

Blanke, C.D., "Celecoxib With Chemotherapy in Colorectal Cancer," *Oncology (Huntingt)* 16(No. 4 Suppl. 3):17-21 (Apr. 2002).

Boirivant, M. et al., "Lamina Propria T Cells in Crohn's Disease and Other Gastrointestinal Inflammation Show Defective CD2 Pathway-Induced Apoptosis," *Gastroenterology 116*:557-565, American Gastroenterological Association (1999).

Cao, S.-G. et al., "Novel Cytotoxic Polyprenylated Xanthonoids from *Garcinia gaudichaudii* (Guttiferae)," *Tetrahedron 54*:10915-10924, Elsevier Science Ltd. (1998).

Cao, S.-G. et al., "Cytotoxic Caged Tetraprenylated Xanthonoids from *Garcinia gaudichaudii* (Guttiferae)," *Tetrahedron Lett. 39*:3353-3356, Elsevier Science Ltd. (1998).

Chinnaiyan, A.M. et al., "The inhibition of pro-apoptotic ICE-like proteases enhances HIV replication," *Nat. Med. 3*:333-337, Nature Publishing Company (1997).

Coven, T.R. et al., "PUVA-induced lymphocyte apoptosis: Mechanism of action in psoriasis," *Photodermatol. Photoimmunol. Photomed. 15*:22-27, Blackwell Munksgaard (1999).

Crawford, K.W. and Bowen, W.D., "Sigma-2 Receptor Agonists Activate a Novel Apoptotic Pathway and Potentiate Antineoplastic (Continued)

*Primary Examiner*—Kamal A Saeed
*Assistant Examiner*—Janet L Coppins
(74) *Attorney, Agent, or Firm*—Sterne, Kessler, Goldstein & Fox P.L.L.C.

(57) ABSTRACT

The present invention is directed to novel derivatives of gambogic acid and analogs thereof. The present invention also relates to the discovery that novel derivatives of gambogic acid are activators of caspases and inducers of apoptosis. Therefore, the activators of caspases and inducers of apoptosis of this invention can be used to induce cell death in a variety of clinical conditions in which uncontrolled growth and spread of abnormal cells occurs.

4 Claims, No Drawings

OTHER PUBLICATIONS

Drugs in Breast Tumor Cell Lines," *Can. Res. 62*:313-322, American Association for Cancer Research, Inc. (Jan. 2002).

Database Biosis, Accession No. PREV199191109495, Qu, B.-X. et al., "The Experimental Studies on Antineoplastic Action of Gambogic II," one page (1991).

Giermasz, A. et al., "Potentiating Antitumor Effects of a Combination Therapy with Lovastatin and Butyrate in the Lewis Lung Carcinoma Model in Mice," *Int. J. Cancer 97*:746-750, Wiley-Liss, Inc. (Feb. 2002).

Heenen, M. et al., "Methotrexate induces apoptotic cell death in human keratinocytes," *Arch. Dermatol. Res. 290*:240-245, Springer-Verlag (1998).

Infante, A.J. et al., "The clinical spectrum in a large kindred with autoimmune lymphoproliferative syndrome caused by a Fas mutation that impairs lymphocyte apoptosis," *J. Pediatr. 133*:629-633, Mosby, Inc. (1998).

Kalemkerian, G.P. and Ou, X., "Activity of fenretinide plus chemotherapeutic agents in small-cell lung cancer cell lines," *Cancer Chemother. Pharmacol. 43*:145-150, Springer-Verlag (1999).

Karanjgaonkar, C.G. et al., "Morellic, Isomorellic and Gambogic Acids," *Tetrahedron Letts. 7*:687-691, Pergamon Press Ltd. (1966).

Kelland, L.R. et al., "Preclinical Antitumor Activity and Pharmacodynamic Studies with the Farnesyl Protein Transferase Inhibitor R115777 in Human Breast Cancer," *Clin. Cancer Res. 7*:3544-3550, American Association for Cancer Research, Inc. (2001).

Kyprianou, N. and Benning, C.M., "Suppression of Human Prostate Cancer Cell Growth By α1-Adrenoceptor Antagonists Doxazosin and Terazosin via Induction of Apoptosis," *Cancer Res. 60*:4550-4555, American Association for Cancer Research, Inc. (2000).

Leong, Y.-W. et al., "Forbesione, a Modified Xanthone from *Garcinia forbesii*," *J. Chem. Res.* (S).:392-393, The Royal Society of Chemistry (1996).

Lin, L.-J. et al., "Isogambogic Acid and Isomorellinol from *Garcinia hanburyi*," *Magn. Reson. Chem. 31*:340-347, John Wiley & Sons, Ltd. (1993).

Liu, W.M. et al., "The in vitro activity of the tyrosine kinase inhibitor ST1571 in BCR-ABL positive chronic myeloid leukaemia cells: synergistic interactions with anti-leukaemic agents," *Br. J. Cancer 86*:1472-1478, Nature Publishing Group (May 2002).

López-Hoyos, M. et al., "Regulation of B cell apoptosis by Bcl-2 and Bcl-$X_L$ and its role in the development of autoimmune diseases (Review)," *Int. J. Mol. Med. 1*:475-483, D. A. Spandidos (1998).

Lu, G.B. et al., "Isolation and Structure of Neo-gambogic Acid from Gamboge (*Garcinia hanburryi*)," *Yao Hsueh Hsueh Pao 19*:636-639, The Chinese Pharmaceutical Association and The Institute of Materia Medica (1984).

Motwani, M. et al., "Augmentation of Apoptosis and Tumor Regression by Flavopiridol in the Presence of CPT-11 in Hct116 Colon Cancer Monolayers and Xenografts," *Clin. Cancer Res. 7*:4209-4219, American Association for Cancer Research, Inc. (2001).

Ohsako, S. and Elkon, K.B., "Apoptosis in the effector phase of autoimmune diabetes, multiple sclerosis and thyroiditis," *Cell Death Differ. 6*:13-21, Nature Publishing Group (1999).

Ollis, W.D. et al., "The Constitution of Gambogic Acid," *Tetrahedron 21*:1453-1470, Pergamon Press Ltd. (1965).

O'Reilly, L.A. & Strasser, A., "Review: Apoptosis and autoimmune disease," *Inflamm. Res. 48*:5-21, Birkhäuser Verlag, Basel (1999).

Ozawa, M. et al., "312-nanometer Ultraviolet B Light (Narrow-Band UVB) Induces Apoptosis of T Cells within Psoriatic Lesions," *J. Exp. Med. 189*:711-718, The Rockefeller University Press (1999).

Qu, B.-X. et al., "The Experimental Studies on Antineoplastic Action of Gambogic II," *Zhongguo Zhongliu Linchuang 18*:50-52, Tianjin: Tianjin-shi Yixue Zazhi She (1991).

Rao, G.S.R. et al., "Structure of moreollin, a pigment isolated from *Garcinia morella* Desser," *Proc. Indian Acad. Sci. 87A*:75-86, The Indian Academy of Sciences (1978).

Regar, E. et al., "Stent development and local drug delivery," *Br. Med. Bull. 59*:227-248, Oxford University Press (2001).

Rukachaisirikul, V. et al., "Caged-Tetraprenylated Xanthones from *Garcinia scortechinii*," *Tetrahedron 56*:8539-8543, Elsevier Science Ltd. (2000).

Savill, J., "Apoptosis in resolution of inflammation," *J. Leukoc. Biol. 61*:375-380, Society for Leukocyte Biology (1997).

Sgadari, C. et al., "HIV protease inhibitors are potent anti-angiogenic molecules and promote regression of Kaposi sarcoma," *Nat. Med. 8*:225-232, Nature America Inc. (Mar. 2002).

Tai, D.-I. et al., "Activation of Nuclear Factor κB in Hepatitis C Virus Infection: Implications for Pathogenesis and Hepatocarcinogenesis," *Hepatology 31*:656-664, W.B. Saunders Company (2000).

Thoison, O. et al., "Cytotoxic Prenylxanthones from *Garcinia bracteata*," *J. Nat. Prod. 63*:441-446, American Chemical Society (2000).

Vaishnaw, A.K. et al., "The molecular basis for apoptotic defects in patients with CD95 (Fas/Apo-1) mutations," *J. Clin. Invest. 103*:355-363, The American Society for Clinical Investigation Inc. (1999).

Vilner, B.J. et al., "Sigma-1 and Sigma-2 Receptors Are Expressed in a Wide Variety of Human and Rodent Tumor Cell Lines," *Cancer Res. 55*:408-413, American Association for Cancer Research, Inc. (1995).

Wakisaka, S. et al., "Modulation by proinflammatory cytokines of Fas/Fas ligand-mediated apoptotic cell death of synovial cells in patients with rheumatoid arthritis (RA)," *Clin. Exp. Immunol. 114*:119-128, Blackwell Science Ltd. (1998).

Wu, J. et al., "A highly rearranged tetraprenylxanthonoid from *Garcinia gaudichaudii* (Guttiferae)," *Tetrahedron Lett. 42*:727-729, Elsevier Science Ltd. (2001).

Wu, X. et al., "Mitochondrial Destabilisation and Caspase-3 Activation are Involved in the Apoptosis of Jurkat Cells Induced by Gaudichaudione A, a Cytotoxic Xanthone," *Planta Med. 68*:198-203, Georg Thieme Verlag Stuttgart (Mar. 2002).

Xu, Y.J. et al., "Novel Cytotoxic, Polyprenylated Heptacyclic Xanthonoids from Indonesian *Garcinia gaudichaudii* (Guttiferae)," *Organic Lett. 2*:3945-3948, American Chemical Society (2000).

Zhou, T. et al., "Bisindolylmaleimide VIII facilitates Fas-mediated apoptosis and inhibits cell-mediated autoimmune diseases," *Nat. Med. 5*:42-48, Nature America Inc. (1999).

Zou, C. et al., "Combined effect of chemopreventive agent N-(4-hydroxyphenyl) retinamide (4-HPR) and γ-radiation on bladder cancer cell lines," *Int. J. Oncol. 13*:1037-1041, D. A. Spandidos (1998).

\* cited by examiner

DERIVATIVES OF GAMBOGIC ACID AND ANALOGS AS ACTIVATORS OF CASPASES AND INDUCERS OF APOPTOSIS

STATEMENT REGARDING FEDERALLY-SPONSORED RESEARCH AND DEVELOPMENT

This invention was made in part with government support under DHHS Grant No. 1R43 CA91811-01 awarded by the National Cancer Institute. The U.S. Government has certain rights to the invention.

BACKGROUND OF THE INVENTION

1. Field of the Invention

This invention is in the field of medicinal chemistry. In particular, the invention relates to derivatives of gambogic acid and analogs, and the discovery that these compounds are activators of caspases and inducers of apoptosis. The invention also relates to the use of these compounds as therapeutically effective anti-cancer agents.

2. Description of Background Art

Organisms eliminate unwanted cells by a process variously known as regulated cell death, programmed cell death or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane-enclosed particles containing intracellular material) (Orrenius, S., *J. Internal Medicine* 237:529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally-encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases are a key element in apoptosis (see, e.g. Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the proapoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become immortal—they become cancerous. In the case of the apoptosis process, control points are known to exist that represent points for intervention leading to activation. These control points include the CED-9—BCL-like and CED-3—ICE-like gene family products, which are intrinsic proteins regulating the decision of a cell to survive or die and executing part of the cell death process itself, respectively (Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los et al., *Blood*, 90(8):3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_0$. During multiplication, cells progress to a stage in which DNA synthesis occurs, termed S. Later, cell division, or mitosis, occurs in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many slow growing tumors, e.g. colon cancers, exist primarily in the $G_0$ phase, whereas rapidly proliferating normal tissues, e.g. bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically-effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

Gambogic acid was isolated from gamboge and the structure was deduced from the $^1$H NMR spectrum and by comparison with morellin, which also has the xanthone structure as that of gambogic acid (Ahmad, S. A., et al. *J. Chem. Soc.* (C) 772-779 (1966); Ollis, W. D., et al. *Tetrahedron,* 21:1453-1470 (1965)).

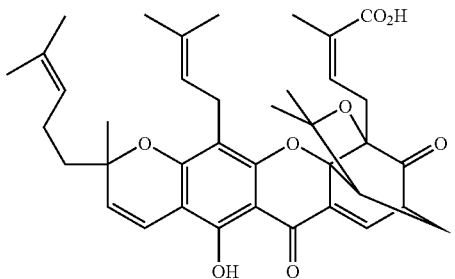

Asano J., et al., *Phytochemistry,* 41:815-820 (1996), reported the isolation of several xanthones, including gambogic acid from gamboge. They reported that gambogic acid is cytotoxic to both HeLa and HEL cells.

Lin, L.-J., et al., *Magn. Reson. Chem.* 31:340-347 (1993), reported the isolation of gambogic acid, as well as isogambogic acid and isomorellinol. All 3 compounds were reported to be cytotoxic against KB and KB-V1 cell lines.

WO00/44216 disclosed gambogic acid, analogs and derivatives as activators of caspases and inducers of apoptosis.

SUMMARY OF THE INVENTION

The present invention is related to the discovery that derivatives of gambogic acid and analogs are activators of the caspase cascade and inducers of apoptosis. Therefore, the first aspect of the present invention is directed to the use of derivatives of gambogic acid and analogs as inducers of apoptosis.

A second aspect of the present invention is directed to a method of treating, preventing or ameliorating a disorder responsive to the induction of apoptosis in an animal suffering therefrom, comprising administering to a mammal in need of such treatment an effective amount of a derivative of gambogic acid or analog thereof, or pharmaceutically acceptable salts or prodrugs thereof.

A third aspect of the present invention is to provide a method for treating, preventing or ameliorating neoplasia and cancer by administering a derivative of gambogic acid or analog thereof to a mammal in need of such treatment.

A fourth aspect of the present invention is to provide novel derivatives of gambogic acid and analogs, and to also provide for the use of these novel compounds for treating, preventing or ameliorating neoplasia and cancer.

A fifth aspect of the present invention is to provide a pharmaceutical composition useful for treating disorders responsive to the induction of apoptosis, containing an effective amount of a derivative of gambogic acid or analog thereof in admixture with one or more pharmaceutically acceptable carriers or diluents.

A sixth aspect of the present invention is directed to methods for the preparation of novel derivatives of gambogic acid and analogs.

DETAILED DESCRIPTION OF THE INVENTION

The present invention arises out of the discovery that derivatives of gambogic acid are potent and highly efficacious activators of the caspase cascade and inducers of apoptosis. Therefore, these compounds are useful for treating disorders responsive to induction of apoptosis.

There are many functional groups in the structure of gambogic acid that can be modified. These include, but are not limited to, the carboxyl group, which can be converted to an ester, amide, ketone or alcohol and other functional groups. The ester and amide can also contain other functional groups, such as a carboxyl in an amino acid, for further modification; the hydroxy group, which can be converted to an ether or ester and other functional groups; the carbon-carbon double bond in the α,β-unsaturated ketone, which can react with a nucleophile, or be reduced to a carbon-carbon single bond, or be converted to an epoxide, and undergo other reactions; the carbon-carbon double bond in the α,β-unsaturated carboxyl, which also can react with a nucleophile, or be reduced to a carbon-carbon single bond, or be converted to a cyclopropane ring, and undergo other reactions; the two isoprene carbon-carbon double bonds, which can be reduced to a carbon-carbon single bond, or be converted to an epoxide, which can then undergo other reactions, or be cleaved to form an aldehyde or carboxyl group, which also can be modified to other functional groups; the carbon-carbon double bond in the left ring also can be reduced to a carbon-carbon single bond, or be converted to an epoxide, and undergo other reactions; the ketone group in the right ring can be reduced to an alcohol, or be converted to an oxime or a semicarbazone, or be converted to an amino group; the other ketone group also can be reduced, or be converted to other functional groups. Therefore, many derivatives of gambogic acid can be prepared.

In addition, analogs of gambogic acid, including isomorellin, morellic acid, desoxymorellin, gambogin, morelline dimethyl acetal, isomoreollin B, Moreollinc acid, gambogenic acid, gambogenin, isogambogenin, desoxygambogenin, gambogenin dimethyl acetal, gambogellic acid, hanburin (Asano, J., et al., *Phytochemistry* 41:815-820 (1996)), isogambogic acid, isomorellinol (Lin, L.-J., et al., *Magn. Reson. Chem.* 31:340-347 (1993)) and neo-gambogic acid (Lu, G. B., et al., *Yao Hsueh Hsueh Pao* 19:636-639 (1984)) can be isolated from gamboge. Other analogs of gambogic acid, including morellin, desoxymorellin, dihydroisomorellin (Bhat et al. *Indian J. Chem.* 2:405-409 (1964)) and moreollin (Rao et al. *Proc. Indian Acad. Sci.* 87A:75-86 (1978)) can be isolated from the seed of *Garcinia morella*. Morellinol can be isolated from the bark of *Garcinia morella* (Adawadkar et al. *Indian J. Chem.* 14B:19-21 (1976)). Gaudichaudiones (A-H) and gaudichaudiic acids (A-E) can be isolated from the leaves of *garcinia Gaudichaudii* (Guttiferae) (Cao, S. G., et al., *Tetrahedron* 54(36):10915-10924 (1998), Cao, S. G., et al., *Tetrahedron Lett.* 39(20):3353-3356 (1998), and Wu, X. et al., *Planta Med.* 68:198-203, (2002)). Forbesione can be isolated from *Garcinia forbesii* (Leong, Y. W., et al., *J. Chem. Res., Synop.* 392-393 (1996)). Bractatin, isobractatin, 1-0-methylbractatin, 1-0-methylisobractatin, 1-0-methyl-8-methoxy-8,8a-dihydrobractatin, and 1-0-methylneobractatin can be isolated from a leaf extract of *G. bracteata* (Thoison, O., et al., *J. Nat. Prod.* 63:441-446 (2000)). Novel gaudichaudiic acids (F-I) can be isolated from the bark of Indonesian *Garcinia gaudichaudil* Xu, Y., et al., *Organic Lett.* 2(24):3945-3948 (2000)). Scortechinones (A-C) can be isolated from twigs of *Garcinia scortechinii* (Rukachaisirikul, V., et al., *Tetrahedron* 56:8539-8543 (2000)). Gaudispirolactone can be isolated from the bark of *Garcinia gaudichaudii* (Wu, J., et al., *Tetrahedron Lett.* 42:727-729 (2001)). These gambogic acid analogs also can be used for the preparation of derivatives similar to gambogic acid.

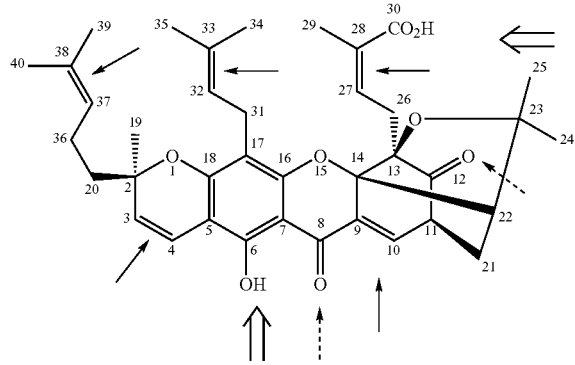

The present invention, therefore, also arises out of the discovery that novel derivatives of gambogic acid analogs are activators of the caspase cascade and inducers of apoptosis. Therefore, these derivatives and analogs of gambogic acid are useful for treating disorders responsive to the induction of apoptosis.

Specifically, compounds useful in this aspect of the present invention are derivatives of gambogic acid and its analogs, or pharmaceutically acceptable salts or prodrugs thereof.

Exemplary preferred compounds that may be employed in the method of invention include, without limitation:
2-(Morpholin-4-yl)-ethyl gambogate;
2-Dimethylaminoethyl gambogate;
N-[3-(4-Methyl-piperazin-1-yl)-propyl]gambogamide;
N-(3-Morpholin-4-yl-propyl)gambogamide;
Methyl 37,38-Dihydroxy-gambogate;
Methyl 37,38-Dihydroxy-9,10-dihydro-10-morpholinyl-gambogate;
Methyl 20-Ethylaldehyde-9,10-dihydro-10-morpholinyl-morellinate;
N-(4-Azido-2,3,5,6-tetrafluoro-benzyl)gambogamide;
N-(1,2-Dicarboxylethyl)gambogamide; and
N-(4-Azidobenzohydrazide)gambogamide.

The positions in gambogic acid are numbered according to Asano, J., et al., *Phytochemistry* 41:815-820 (1996), and Lin, L.-J., et al., *Magn. Reson. Chem.* 31:340-347 (1993).

The present invention is also directed to novel derivatives of gambogic acid and analogs. Exemplary preferred compounds that may be employed in this invention include, without limitation:
2-(Morpholin-4-yl)-ethyl gambogate;
2-Dimethylaminoethyl gambogate;
N-[3-(4-Methyl-piperazin-1-yl)-propyl]gambogamide;
N-(3-Morpholin-4-yl-propyl)gambogamide;
Methyl 37,38-Dihydroxy-gambogate;
Methyl 37,38-Dihydroxy-9,10-dihydro-10-morpholinyl-gambogate;
Methyl 20-Ethylaldehyde-9,10-dihydro-10-morpholinyl-morellinate;
N-(4-Azido-2,3,5,6-tetrafluoro-benzyl)gambogamide;
N-(1,2-Dicarboxylethyl)gambogamide; and
N-(4-Azidobenzohydrazide)gambogamide.

Certain of the compounds of the present invention may exist as stereoisomers including optical isomers. The invention includes all stereoisomers and both the racemic mixtures of such stereoisomers, as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g. those obtained by condensation with a $C_{1-4}$ alcohol according to methods known in the art); esters of hydroxy containing compounds (e.g. those obtained by condensation with a $C_{1-4}$ carboxylic acid, $C_{3-6}$ dioic acid or anhydride thereof (e.g. succinic and fumaric anhydrides according to methods known in the art); imines of amino containing compounds (e.g. those obtained by condensation with a $C_{1-4}$ aldehyde or ketone according to methods known in the art); and acetals and ketals of alcohol containing compounds (e.g. those obtained by condensation with chloromethyl methyl ether or chloromethyl ethyl ether according to methods known in the art).

The compounds of this invention may be prepared using methods known to those skilled in the art, or the novel methods of this invention. Specifically, novel derivatives of gambogic acid can be prepared as illustrated by exemplary reactions in Scheme 1. Reaction of gambogic acid with an amine, such as 3-(4-methyl-piperazin-1-yl)-propylamine, in the presence of dimethylaminopyridine (DMAP) and a coupling reagent, such as 1-(3-dimethylamino-propyl)-3-ethyl-carbodiimide hydrochloride (EDCI), produced the amide product.

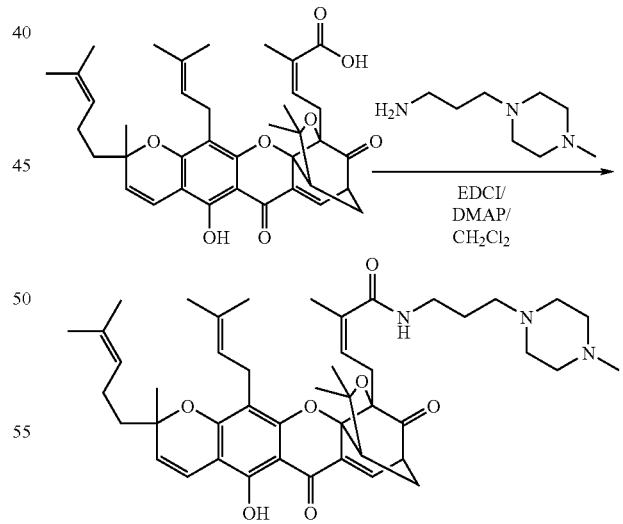

Scheme 1

Novel derivatives of gambogic acid can also be prepared as illustrated by exemplary reactions in Scheme 2. Reaction of gambogic acid with an alkylhalide, such as 4-(2-chloroethyl)morpholine, in the presence of a base, such as potassium carbonate, produced the ester product. These novel derivatives of gambogic acid are designed to increase the aqueous solubility of the compounds.

Scheme 2

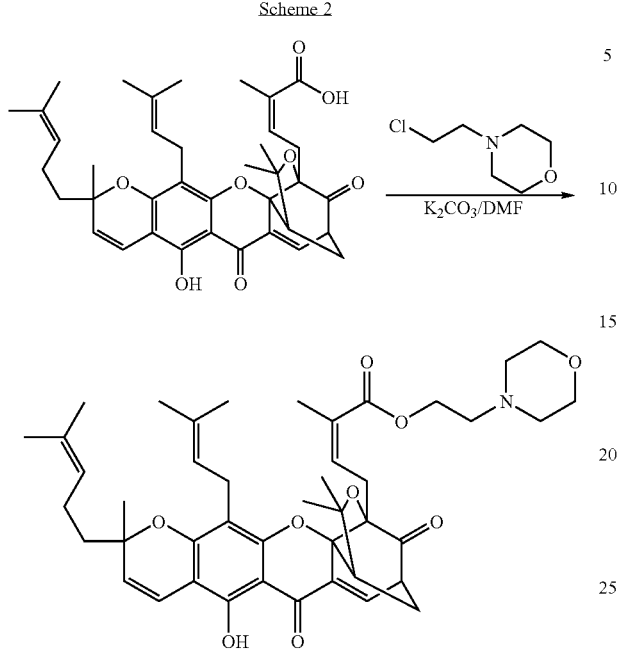

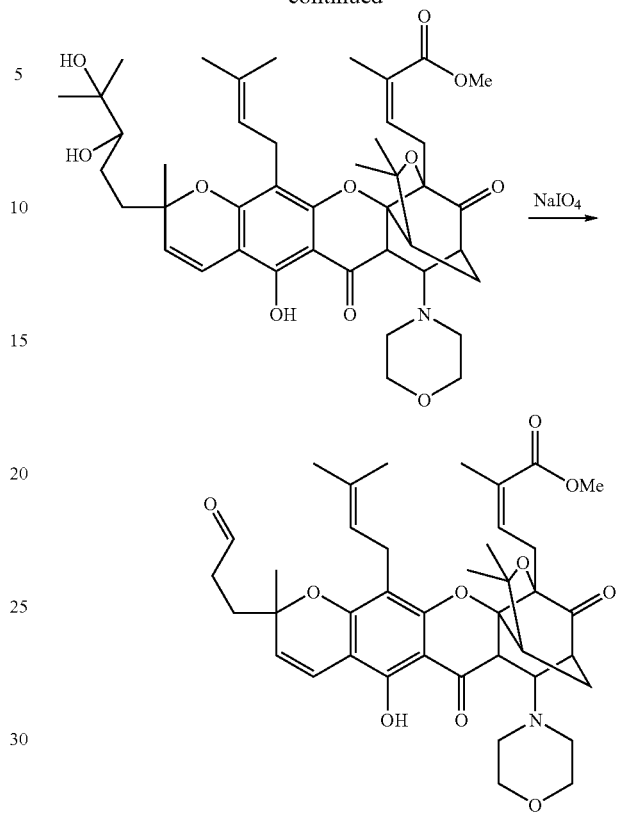

Novel derivatives of gambogic acid can also be prepared as illustrated by exemplary reactions in Scheme 3. Reaction of methyl gambogate with osmium tetroxide in the presence of N-methylmorpholine N-oxide resulted in the selective oxidation of the 37,38 double bond to give the 37,38-dihydroxy derivative. Reaction of the 37,38-dihydroxy derivative with morpholine produced the 10-morpholinyl adduct. Oxidation of the 10-morpholinyl adduct by $NaIO_4$ in THF produced the aldehyde derivative.

Scheme 3

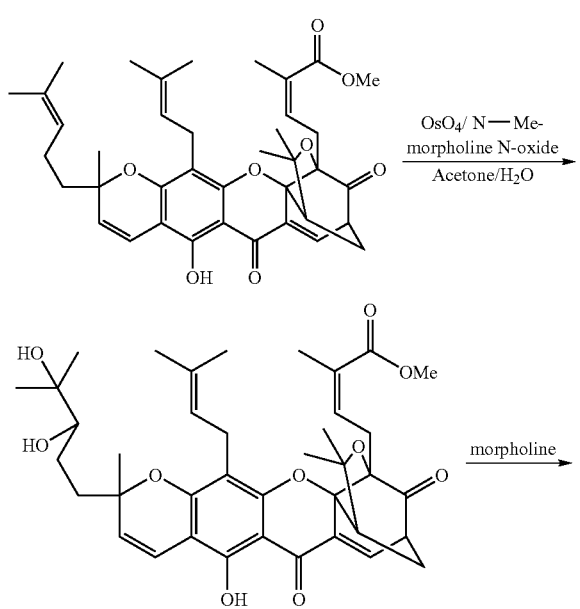

An important aspect of the present invention is the discovery that novel derivatives of gambogic acid are activators of caspases and inducers of apoptosis. Therefore, these compounds are expected to be useful in a variety of clinical conditions in which there is uncontrolled cell growth and spread of abnormal cells, such as in the case of cancer.

Yet another important aspect of the present invention is the discovery that the compounds described herein are potent and highly efficacious activators of caspases and inducers of apoptosis in drug resistant cancer cells, such as breast and prostate cancer cells, which enables these compounds to kill drug resistant cancer cells. In comparison, most standard anticancer drugs are not effective in killing drug resistant cancer cells under the same conditions. Therefore, gambogic acid, its derivatives and analogs, are expected to be useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of a compound described herein, which functions as a caspase cascade activator and inducer of apoptosis.

The present invention also includes a therapeutic method comprising administering to an animal an effective amount of a compound, or a pharmaceutically acceptable salt or prodrug of said novel derivatives of gambogic acid, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute and chronic lymphocytic leukemias, multiple myeloma, neuroblastoma, breast carcinomas, ovarian carcinomas, lung carcinomas, Wilms' tumor, cervical carcinomas, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In practicing the therapeutic methods, effective amounts of compositions containing therapeutically effective concentrations of the compounds formulated for oral, intravenous, local and topical application (for the treatment of neoplastic diseases and other diseases in which caspase cascade mediated physiological responses are implicated), are administered to an individual exhibiting the symptoms of one or more of these disorders. The amounts are effective to ameliorate or eliminate one or more symptoms of the disorder. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms.

In another embodiment, a pharmaceutical composition comprising a compound, or a pharmaceutically acceptable salt of a compound described herein, which functions as a caspase cascade activator and inducer of apoptosis in combination with a pharmaceutically acceptable vehicle, is provided.

Another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known cancer chemotherapeutic agent, or a pharmaceutically acceptable salt of said agent. Examples of known anti-cancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy, include arsenic trioxide, gemcitabine, melphalan, chlorambucil, cyclophosamide, ifosfamide, vincristine, mitoguazone, epirubicin, aclarubicin, bleomycin, mitoxantrone, elliptinium, fludarabine, ocreotide, retinoic acid, tamoxifen and alanosine.

In practicing the methods of the present invention, the compound of the invention may be administered together with the at least one known chemotherapeutic agent as part of a unitary pharmaceutical composition. Alternatively, the compound of the invention may be administered apart from the at least one known cancer chemotherapeutic agent. In this embodiment, the compound of the invention and the at least one known cancer chemotherapeutic agent are administered substantially simultaneously, i.e. the compounds are administered at the same time or one after the other, so long as the compounds reach therapeutic levels for a period of time in the blood.

It has been reported that alpha-1-adrenoceptor antagonists, such as doxazocin, terazosin, and tamsulosin can inhibit the growth of prostate cancer cell via induction of apoptosis (Kyprianou, N., et al., *Cancer Res* 60:4550-4555, (2000)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known alpha-1-adrenoceptor antagonists, or a pharmaceutically acceptable salt of said agent. Examples of known alpha-1-adrenoceptor antagonists, which can be used for combination therapy include, but are not limited to, doxazocin, terazosin, and tamsulosin.

It has been reported that Sigma-2 receptors are expressed in high densities in a variety of tumor cell types (Vilner, B. J., et al., *Cancer Res.* 55: 408-413 (1995)) and that sigma-2 receptor agonists, such as CB-64D, CB-184 and haloperidol activate a novel apoptotic pathway and potentiate antineoplastic drugs in breast tumor cell lines. (Kyprianou, N., et al., *Cancer Res.* 62:313-322 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known sigma-2 receptor agonists, or a pharmaceutically acceptable salt of said agent. Examples of known sigma-2 receptor agonists, which can be used for combination therapy include, but are not limited to, CB-64D, CB-184 and haloperidol.

It has been reported that combination therapy with lovastatin, a HMG-CoA reductase inhibitor, and butyrate, an inducer of apoptosis in the Lewis lung carcinoma model in mice, showed potentiating antitumor effects (Giermasz, A., et al., *Int. J. Cancer* 97:746-750 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known HMG-CoA reductase inhibitor, or a pharmaceutically acceptable salt of said agent. Examples of known HMG-CoA reductase inhibitors, which can be used for combination therapy include, but are not limited to, lovastatin, simvastatin, pravastatin, fluvastatin, atorvastatin and cerivastatin.

It has been reported that HIV protease inhibitors, such as indinavir or saquinavir, have potent anti-angiogenic activities and promote regression of Kaposi sarcoma (Sgadari, C., et al., *Nat. Med.* 8:225-232 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known HIV protease inhibitor, or a pharmaceutically acceptable salt of said agent. Examples of known HIV protease inhibitors, which can be used for combination therapy include, but are not limited to, amprenavir, abacavir, CGP- 73547, CGP-61755, DMP-450, indinavir, nelfinavir, tipranavir, ritonavir, saquinavir, ABT-378, AG 1776, and BMS-232,632.

It has been reported that synthetic retinoids, such as fenretinide (N-(4-hydroxyphenyl)retinamide, 4HPR), have good activity in combination with other chemotherapeutic agents, such as cisplatin, etoposide or paclitaxel in small-cell lung cancer cell lines (Kalemkerian, G. P., et al., *Cancer Chemother. Pharmacol.* 43:145-150 (1999)). 4HPR also was reported to have good activity in combination with gamma-radiation on bladder cancer cell lines (Zou, C., et al., *Int. J. Oncol.* 13:1037-1041 (1998)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known retinoid and synthetic retinoid, or a pharmaceutically acceptable salt of said agent. Examples of known retinoids and synthetic retinoids, which can be used for combination therapy include, but are not limited to, bexarotene, tretinoin, 13-cis-retinoic acid, 9-cis-retinoic acid, α-difluoromethylornithine, ILX23-7553, fenretinide, and N-4-carboxyphenyl retinamide.

It has been reported that proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., *Leukemia* 16:433-443 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known proteasome inhibitor, or a pharmaceutically acceptable salt of said agent. Examples of known proteasome inhibitors, which can be used for combination therapy include, but are not limited to, lactacystin, MG-132, and PS-341.

It has been reported that tyrosine kinase inhibitors, such as STI571 (Imatinib mesilate, Gleevec), have potent synergetic effect in combination with other anti-leukemic agents, such as etoposide (Liu, W. M., et al. *Br. J. Cancer* 86:1472-1478 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known tyrosine kinase inhibitor, or a pharmaceutically acceptable salt of said agent. Examples of known tyrosine kinase inhibitors, which can be used for combination therapy include, but are not limited to, gleevec, ZD1839 (Iressa), SH268, genistein, CEP2563, SU6668, SU11248, and EMD121974.

It has been reported that prenyl-protein transferase inhibitors, such as farnesyl protein transferase inhibitor R115777, possess preclinical antitumor activity against human breast cancer (Kelland, L. R., et. al., *Clin. Cancer Res.* 7:3544-3550 (2001)). Synergy of the protein farnesyltransferase inhibitor SCH66336 and cisplatin in human cancer cell lines also has been reported (Adjei, A. A., et al., *Clin. Cancer. Res.* 7:1438-1445 (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known prenyl-protein transferase inhibitor, including farnesyl protein transferase inhibitor, inhibitors of geranylgeranyl-protein transferase type I (GGPTase-I) and geranylgeranyl-protein transferase type-II, or a pharmaceutically acceptable salt of said agent. Examples of known prenyl-protein transferase inhibitors, which can be used for combination therapy include, but are not limited to, R115777, SCH66336, L-778, 123, BAL9611 and TAN-1813.

It has been reported that cyclin-dependent kinase (CDK) inhibitors, such as flavopiridol, have potent synergetic effect in combination with other anticancer agents, such as CPT-11, a DNA topoisomerase I inhibitor in human colon cancer cells (Motwani, M., et al., *Clin. Cancer Res.* 7:4209-4219, (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known cyclin-dependent kinase inhibitor, or a pharmaceutically acceptable salt of said agent. Examples of known cyclin-dependent kinase inhibitor, which can be used for combination therapy include, but are not limited to, flavopiridol, UCN-01, roscovitine and olomoucine.

It has been reported that in preclinical studies COX-2 inhibitors were found to block angiogenesis, suppress solid tumor metastases, and slow the growth of implanted gastrointestinal cancer cells (Blanke, C. D., *Oncology (Huntingt)* 16 (No. 4 Suppl. 3):17-21 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known COX-2 inhibitors, or a pharmaceutically acceptable salt of said agent. Examples of known COX-2 inhibitors, which can be used for combination therapy include, but are not limited to, celecoxib, valdecoxib, and rofecoxib.

Another embodiment of the present invention is directed to a composition effective to inhibit neoplasia comprising a bioconjugate of a compound described herein, which functions as a caspase cascade activator and inducer of apoptosis, in bioconjugation with at least one known therapeutically useful antibody, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of a compound described herein, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thymocytes in Hashimoto's thyroiditis (Ohsako, S., et al., *Cell Death Differ.* 6(1):13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr.* 133(5):629-633 (1998) and Vaishnaw, A. K., et al., *J. Clin. Invest.* 103(3):355-363 (1999)). It was reported that overexpression of Bcl-2, which is a member of the Bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1(2):475-483 (1998)). It is therefore, evident that many types of autoimmune disease are caused by defects of the apoptotic process and one treatment strategy would be to turn on apoptosis in the lymphocytes that are causing autoimmmune disease (O'Reilly, L. A. & Strasser, A., *Inflamm. Res.* 48(1):5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., *J. Immunol.* 162(1):603-608 (1999)) reported that by direct injection of DNA expression vectors encoding FasL into the inflamed thyroid, the development of lymphocytic infiltration of the thyroid was inhibited and induction of the death of infiltrating T cells was observed. These results show that FasL expression on thymocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. (Zhou, T., et al, *Nat. Med.* 5(1):42-8 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of a compound described herein, which functions as a caspase cascade activator and inducer of apoptosis, should be an effective treatment for autoimmune disease.

Psoriasis is a chronic skin disease, which is characterized by scaly red patches. Psoralen plus ultraviolet A (PUVA) is a widely used and effective treatment for psoriasis vulgaris and Coven, T. R., et al., *Photodermatol. Photoimmunol. Photomed.* 15(1):22-7 (1999), reported that lymphocytes treated with psoralen 8-MOP or TMP plus UVA displayed DNA degradation patterns typical of apoptotic cell death. Ozawa, M., et al., *J. Exp. Med.* 189(4):711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, M., et al., *Arch. Dermatol. Res.* 290(5):240-245 (1998), reported that low doses of methotrexate may induce apoptosis and this mode of action could explain the reduction in epidermal hyperplasia during treatment of psoriasis with methotrexate. Therefore, an effective amount of a compound, or a pharmaceutically acceptable salt or prodrug of a compound described herein, which functions as a caspase cascade activator and inducer of apoptosis, should be an effective treatment for psoriasis.

Synovial cell hyperplasia is a characteristic of patients with rheumatoid arthritis (RA). Excessive proliferation of RA synovial cells that, in addition, are defective in synovial cell death might be responsible for the synovial cell hyperplasia. Wakisaka, S., et al., *Clin. Exp. Immunol.* 114(1):119-28 (1998), found that, although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells and lead to pannus formation and the destruction of joints in patients with RA. Therefore, an effective amount of a compound, or a pharmaceutically acceptable salt or prodrug of a compound described herein, which functions as a caspase cascade activator and inducer of apoptosis, should be an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61(4):375-80 (1997)). Boirivant, M., et al., *Gastroenterology* 116(3):557-65 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue, indicate that this defect is accompanied by elevated Bcl-2 levels. Therefore an effective amount of a compound, or a pharmaceutically acceptable salt or prodrug of a compound described herein, which functions as a caspase cascade activator and inducer of apoptosis, should be an effective treatment for inflammation.

Caspase cascade activators and inducers of apoptosis may also be a desirable therapy in the elimination of pathogens, such as HIV, Hepatitis C and other viral pathogens. The long lasting quiescence, followed by disease progression, may be explained by an anti-apoptotic mechanism of these pathogens leading to persistent cellular reservoirs of the virions. It has been reported that HIV-1 infected T leukemia cells or peripheral blood mononuclear cells (PBMCs) underwent enhanced viral replication in the presence of the caspase inhibitor Z-VAD-fmk. Furthermore, Z-VAD-fmk also stimulated endogenous virus production in activated PBMCs derived from HIV-1-infected asymptomatic individuals (Chinnaiyan, A., et al., *Nat. Med.* 3:333 (1997)). Therefore, apoptosis may serve as a beneficial host mechanism to limit the spread of HIV and new therapeutics using caspase/apoptosis activators may be useful to clear viral reservoirs from the infected individuals. Similarly, HCV infection also triggers anti-apoptotic mechanisms to evade the host's immune surveillance leading to viral persistence and hepatocarcinogenesis (Tai, D. I., et al. *Hepatology* 3:656-64 (2000)). Therefore, apoptosis inducers may be useful as therapeutics for HIV and other infectious disease.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with anti-proliferative properties are currently under clinical investigation, including actinomycin D, rapamycin or paclitaxel coated stents (Regar E., et al., *Br. Med. Bull.* 59:227-248 (2001)). Therefore, apoptosis inducers, which are antiproliferative, may be useful as therapeutics for in-stent restenosis.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 100 mg/kg, or an equivalent amount of the pharmaceutically acceptable salt thereof, per day of the body weight of the mammal being treated for apoptosis-mediated disorders. The compounds may be administered to mammals, e.g. humans, intravenously at a dose of 0.025 to 200 mg/kg, or an equivalent amount of the pharmaceutically acceptable salt thereof, per day of the body weight of the mammal being treated for apoptosis-mediated disorders. Preferably, approximately 0.01 to approximately 50 mg/kg is orally adminstered to treat or prevent such disorders. For intramuscular injection, the dose is generally approximately one-half of the oral dose. For example, a suitable intramuscular dose would be approximately 0.0025 to approximately 50 mg/kg, and most preferably, from approximately 0.01 to approximately 10 mg/kg. If a known cancer chemotherapeutic agent is also administered, it is administered in an amount which is effective to achieve its intended purpose. The amounts of such known cancer chemotherapeutic agents effective for cancer are well known to those of skill in the art.

The unit oral dose may comprise from approximately 0.01 to approximately 50 mg, preferably approximately 0.1 to approximately 10 mg of the compound of the invention. The unit dose may be administered one or more times daily as one or more tablets, each containing from approximately 0.1 to approximately 10, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that can be used pharmaceutically. Preferably, the preparations, particularly those preparations, which can be administered orally and which can be used for the preferred type of administration, such as tablets, dragees, and capsules, and also preparations, which can be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducer of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducer of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use can be obtained by combining the active compounds with solid excipients, optionally grinding the resultant mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g. maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g. silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethyl-cellulose phthalate, are used. Dye stuffs or pigments may be added to the tablets or dragee coatings, e.g., for identification or in order to characterize combinations of active compound doses.

Other pharmaceutical preparations, which can be used orally, include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally include, e.g. suppositories, which consist of a combination of one or more of the active compounds with a suppository base. Suitable suppository bases are, e.g. natural or synthetic triglycerides, or paraffin hydrocarbons. In addition, it is also possible to use gelatin rectal capsules, which consist of a combination of the active compounds with a base. Possible base materials include, e.g. liquid triglycerides, polyethylene glycols, or paraffin hydrocarbons.

Suitable formulations for parenteral administration include aqueous solutions of the active compounds in water-soluble form, e.g. water-soluble salts and alkaline solutions. In addition, suspensions of the active compounds as appropriate oily injection suspensions may be administered. Suitable lipophilic solvents or vehicles include fatty oils, e.g. sesame oil; or synthetic fatty acid esters, e.g. ethyl oleate or triglycerides or polyethylene glycol-400 (the compounds are soluble in PEG-400). Aqueous injection suspensions may contain substances, which increase the viscosity of the suspension include, e.g. sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes approximately 40 parts water, approximately 20 parts beeswax, approximately 40 parts mineral oil, and approximately 1 part almond oil.

Ointments may be formulated by mixing a solution of the active ingredient in a vegetable oil, such as almond oil with warm soft paraffin and allowing the mixture to cool. A typical example of such an ointment is one which includes approximately 30% almond oil and approximately 70% white soft paraffin by weight.

Also included within the scope of the present invention are dosage forms of the novel derivatives of gambogic acid, in which the oral pharmaceutical preparations comprise an enteric coating. The term "enteric coating" is used herein to refer to any coating over an oral pharmaceutical dosage form that inhibits dissolution of the active ingredient in acidic media, but dissolves rapidly in neutral to alkaline media and has good stability to long-term storage. Alternatively, the dosage form having an enteric coating may also comprise a water soluble separating layer between the enteric coating and the core.

The core of the enterically coated dosage form comprises a novel derivative of gambogic acid. Optionally, the core also comprises pharmaceutical additives and/or excipients. The separating layer may be a water soluble inert compound or polymer for film coating applications. The separating layer is applied over the core by any conventional coating technique known to one of ordinary skill in the art. Examples of separating layers include, but are not limited to sugars, polyethylene glycol, polyvinylpyrrolidone, polyvinyl alcohol, hydroxypropyl cellulose, polyvinyl acetal diethylaminoacetate and hydroxypropyl methylcellulose. The enteric coating is applied over the separating layer by any conventional coating technique. Examples of enteric coatings include, but are not limited to cellulose acetate phthalate, hydroxypropyl methylcellulose phthalate, polyvinyl acetate phthalate, carboxymethylethylcellulose, copolymers of methacrylic acid and methacrylic acid methyl esters, such as Eudragit®L 12,5 or Eudragit®L 100 (R hm Pharma), water based dispersions such as Aquateric® (FMC Corporation), Eudragit®L 100-55 (R hm Pharma) and Coating CE 5142 (BASF), and those containing water soluble plasticizers such as Citroflex® (Pfizer). The final dosage form is either an enteric coated tablet, capsule or pellet.

The following examples are illustrative, but not limiting, of the method and compositions of the present invention. Other suitable modifications and adaptations of the variety of conditions and parameters normally encountered in clinical therapy, and which are obvious to those skilled in the art, are within the spirit and scope of the invention.

Example 1

2-(Morpholin-4-yl)-ethyl gambogate

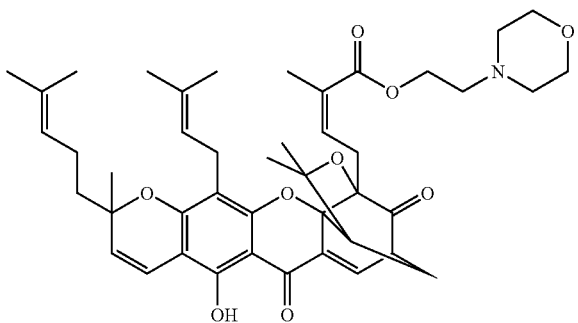

A mixture of gambogic acid (3.77 g, 6 mmol), 4-(2-chloroethyl)morpholine hydrochloride (1.12 g, 6 mmol) and potassium carbonate (1.66 g, 12 mmol) in DMF (40 mL) was stirred at 60° C. for 7 h. It was cooled and diluted with ethyl acetate (50 mL), and the mixture was washed with aqueous ammonium chloride (3×50 mL), dried over $Na_2SO_4$ and evaporated to dryness. The residue was purified by column chromatography ($SiO_2$, Hexane/EtOAc=1:1) to give 2.2 g (50%) of the title compound. $^1$H NMR ($CDCl_3$): 12.85 (s, 1H), 7.54 (d, J=7.2 Hz, 1H), 6.66 (d, J=10.2 Hz, 1H), 6.04 (t, J=6.9 Hz, 1H), 5.43 (d, J=10.2 Hz, 1H), 5.05 (bs, 2H), 4.05-3.95 (m, 2H), 3.65 (t, J=4.5 Hz, 1H), 3.47 (m, 1H), 3.40-2.85 (m, 4H), 2.55-2.40 (m, 6H), 2.34-2.28 (m, 1H), 2.04 (m, 2H), 1.73 (s, 3H), 1.69 (s, 3H), 1.68 (s, 3H), 1.65 (s, 3H), 1.64 (s, 3H), 1.55 (s, 3H), 1.44 (s, 3H), 1.29 (s, 3H).

Example 2

2-Dimethylaminoethyl gambogate

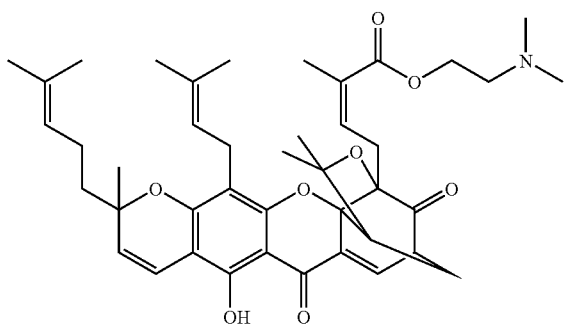

A mixture of gambogic acid (3.170 g, 5.04 mmol), 2-dimethylaminoethyl chloride hydrochloride (0.801 g, 5.56 mmol), potassium iodide (0.43 g, 2.6 mmol) and cesium carbonate (2.031 g, 6.2 mmol) was stirred in a 50° C. oil bath for 40 h under Argon. The reaction mixture was filtered to remove insoluble material, and the solid was washed with EtOAc. The solvent was evaporated under reduced pressure and the residue was partitioned between EtOAc (100 mL) and water (10 mL). The EtOAc phase was separated, dried over $MgSO_4$, and evaporated under reduced pressure. The crude product was purified by chromatography ($SiO_2$, EtOAc:hexanes/15-100%) to give the product as an amber-colored thick oil (3.069 g, 87%): $^1$H NMR ($CDCl_3$) 12.85 (s, 1H), 7.54 (d, J=7.2 Hz, 1H), 6.67 (d, J=10.2 Hz, 1H), 6.05 (m, 1H), 5.43 (d, J=10.2 Hz, 1H), 5.04 (m, 2H), 3.95 (m, 2H), 3.47 (dd, J=4.2, 6.6 Hz, 1H), 3.31 (dd, J=8.1, 14.7 Hz, 1H), 3.14 (m, 1H), 3.05 (ddd, J=1.2, 8.1, 16.5 Hz, 1H), 2.90 (ddd, J=1.5, 6.6, 16.5 Hz, 1H), 2.51 (d, J=9.3 Hz, 1H), 2.41 (t, J=6.3 Hz, 2H), 2.31 (dd, J=4.8, 13.5 Hz, 1H), 2.20 (s, 6H), 2.01 (m, 2H), 1.80 (m 1H), 1.73 (s, 3H), 1.69 (s, 6H), 1.65 (s, 3H), 1.64 (s, 3H), 1.59 (dd, J=2.7, 6.9 Hz, 1H), 1.55 (s, 3H), 1.44 (s, 3H), 1.38 (dd, J=9.3, 12.9 Hz, 1H), 1.28 (s, 3H).

Example 3

N-[3-(4-Methyl-piperazin-1-yl)-propyl]gambogamide

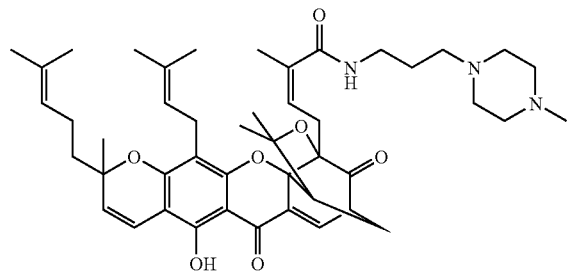

To a solution of 1-(3-dimethylamino-propyl)-3-ethyl-carbodiimide hydrochloride (EDCI) (5.010 g, 2.631 mmol) in anhydrous $CH_2Cl_2$ (40 mL) was added gambogic acid (1.575 g, 2.5 mmol) portionwise at 0° C. under argon, followed by addition of DMAP (15 mg, 0.13 mmol). The orange solution was stirred at 0° C. for 1 h, then 3-(4-methyl-piperazin-1-yl)-propylamine (362 mg, 2.5 mmol) was added slowly. The reaction mixture was stirred at 0° C. for 3.5 h then rt for 2 h. The reaction mixture was quenched with saturated $NaHCO_3$ (10 mL) and the mixture was stirred and separated. The organic phase was dried over $MgSO_4$ and evaporated under reduced pressure. The residue was purified by column chromatography ($SiO_2$, $Et_3$N:EtOAc/5-15%). The product was collected as a yellow solid (0.85 g, 45%): $^1$H NMR ($CDCl_3$) 12.85 (s, 1H), 7.55 (d, J=7.2 Hz, 1H), 6.82 (m, 1H), 6.68 (d, J=10.2 Hz, 1H), 5.45 (d, J=10.2 Hz, 1H), 5.28 (m, 1H), 5.05 (m, 2H), 3.47 (dd, J=4.2 Hz, 6.9 Hz, 1H), 3.35-3.15 (m 5H), 2.75 (dd, J=7.5, 14.7 Hz, 1H), 2.56-2.30 (m, 11H), 2.28 (s, 3H), 2.04 (m, 3H), 1.80 (m, 1H), 1.76 (s, 3H), 1.73 (s, 3H), 1.68 (s, 3H), 1.65 (s, 6H), 1.60 (m, 3H), 1.55 (s, 3H), 1.44 (s, 3H), 1.36 (dd, J=4.5, 8.1 Hz, 1H), 1.28 (s, 3H).

Example 4

N-(3-Morpholin-4-yl-propyl)gambogamide

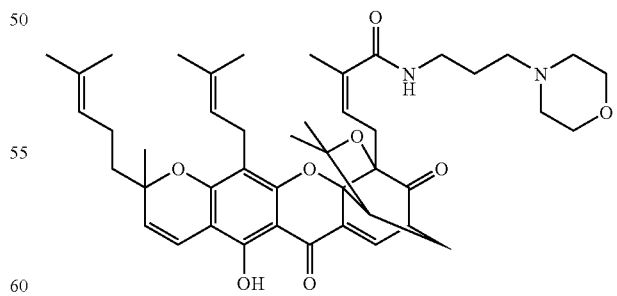

The title compound was prepared by a procedure similar to that of example 3 as a yellow solid from gambogic acid and 3-(morpholin-4-yl)-propylamine: $^1$H NMR ($CDCl_3$) 12.86 (s, 1H), 7.55 (d, J=6.9 Hz, 1H), 6.79 (t, J=5.7 Hz, 1H), 6.68 (d, J=9.9 Hz, 1H), 5.45 (d, J=10.2 Hz, 1H), 5.28 (m, 1H), 5.05

(m, 2H), 3.69 (t, J=4.5 Hz, 4H), 3.47 (dd, J=4.2, 6.6 Hz, 1H), 3.25 (m, 4H), 2.72 (dd, J=8.4, 15.3 Hz, 1H), 2.54-2.29 (m, 9H), 2.32 (m, 2H), 1.80 (m, 1H), 1.76 (s, 3H), 1.73 (s, 3H), 1.68 (m, 5H), 1.65 (s, 6H), 1.59 (dd, J=2.4, 6.6 Hz, 1H), 1.55 (s, 3H), 1.44 (s, 3H), 1.38 (m, 1H), 1.28 (s, 3H).

Example 5

Methyl 37,38-Dihydroxy-gambogate

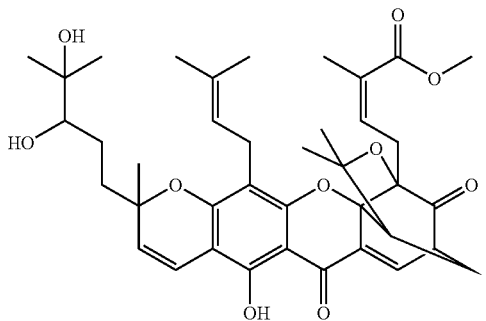

To a solution of methyl gambogate (1.241 g, 1.9 mmol) in acetone:$H_2O$ (9:1, 15 mL) was added N-methylmorpholine N-oxide (0.510 g, 4.4 mmol), followed by addition of osmium tetroxide (2.5% in t-butanol, 0.2 mL, 0.02 mmol). The light brown solution was stirred at rt overnight and additional osmium tetroxide (2 mL, 0.2 mmol) was added. The reaction mixture was stirred at rt for additional 24 h. The reaction mixture was diluted with water (35 mL), and extracted with EtOAc (50 mL, 2×30 mL). The EtOAc solution was washed with brine (10 mL), dried over $MgSO_4$, and evaporated under reduced pressure to give a yellow residue. The crude was purified by column chromatography ($SiO_2$, EOAc:hexanes/ 10-100%) to give the product as a yellow solid (291 mg). $^1H$ NMR ($CDCl_3$) 12.85 (s, 1H), 7.55 (d, J=7.2 Hz, 1H), 6.69 (dd, J=1.8, 10.2 Hz, 1H), 5.98 (m, 1H), 5.44 (d, J=10.2 Hz, 1H), 5.00 (m, 1H), 3.49 (dd, J=4.5, 6.9 Hz, 1H), 3.44 (s, 3H), 3.37-3.27 (m, 3H), 3.20-2.84 (m, 4H), 2.52 (d, J=9.3 Hz, 1H), 2.32 (dd, J=4.8, 13.5 Hz, 1H), 2.18-1.80 (m, 3H), 1.74 (s, 3H), 1.68 (s, 6H), 1.64 (m, 4H), 1.47 (s, 3H), 1.44-1.32 (m, 1H), 1.29 (s, 3H), 1.17 (d, J=9.2 Hz, 3H), 1.11 (d, J=1.8 Hz, 3H); MS 677 (M+1).

Example 6

Methyl 37,38-Dihydroxy-9,10-dihydro-10-morpholinyl-gambogate

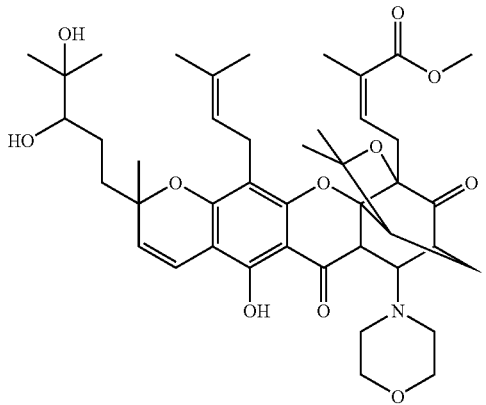

To a solution of methyl 37,38-dihydroxy-gambogate (78 mg, 0.115 mmol) in anhydrous THF (5 mL) under argon, was added morpholine (1 mL) at rt. The yellow solution turned to clear solution instantly. After stirring at rt for 1.5 h, the solvent was evaporated. The residue was dissolved in EtOAc (30 mL), washed with water (3×5 mL), dried over $MgSO_4$, and evaporated. The product was obtained as a light yellow solid (88 mg, 100%; HPLC showed a mixture of two diastereoisomers, 1:1): $^1H$ NMR ($CDCl_3$) 12.0 (s, 1H), 6.67 (dd, J=2.4, 9.9 Hz, 1H), 6.61 (m, 1H), 5.47 (dd, J=3.0, 10.2 Hz, 1H), 4.99 (m, 1H), 3.71-3.55 (m, 8H), 3.37-3.10 (m, 6H), 2.89 (t, J=4.8 Hz, 2H), 2.76 (m, 1H), 2.60-2.40 (m, 4H), 1.99 (m, 1H), 1.95 (d, J=1.2 Hz, 3H), 1.90-1.78 (m, 4H), 1.73 (s, 3H), 1.63 (s, 3H), 1.49 (dd, J=9.0, 14.7 Hz, 1H), 1.37 (d, J=1.8 Hz, 3H), 1.33 (s, 3H), 1.26 (m, 3H), 1.87 (d, J=3.9 Hz, 3H), 1.13 (m, 6H); MS 764 (M+1).

Example 7

Methyl 20-Ethylaldehyde-9,10-dihydro-10-morpholinyl-morellinate

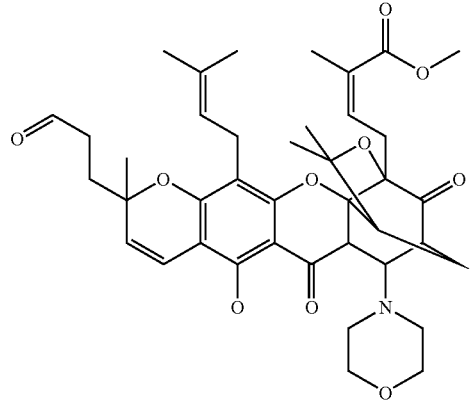

To a solution of methyl 37,38-dihydroxy-9,10-dihydro-10-morpholinyl-gambogate (35 mg, 0.046 mmol) in THF:$H_2O$ (2:1, 1 mL) was added $NaIO_4$ (16 mg, 0.075 mmol). The yellow solution was stirred at rt for 7 h. The reaction mixture was quenched with water (10 mL), extracted with EtOAc (3×10 mL). The EtOAc solution was dried over $MgSO_4$ and evaporated. The crude product was purified by column chromatography ($SiO_2$) to give the product as a yellow solid (12 mg, 38%): $^1H$ NMR ($CDCl_3$) 11.98 (s, 1H), 9.79 (t, J=1.5 Hz, 1H), 6.71 (d, J=9.3 Hz, 1H), 6.60 (dt, J=1.2, 6.6 Hz, 1H), 7.39 (d, J=10.2 Hz, 1H), 4.96 (m, 1H), 3.67 (s, 3H), 3.65-3.54 (m, 4H), 3.32-3.10 (m, 6H), 2.77 (dd, J=3.9, 5.7 Hz, 1H), 2.62-2.51 (m, 5H), 2.46 (m, 2H), 2.18-1.97 (m, 3H), 1.95 (d, J=1.5 Hz, 3H), 1.73 (s, 3H), 1.63 (s, 3H), 1.57 (s, 9H), 1.53-1.43 (m, 2H), 1.39 (s, 3H), 1.36 (s, 3H), 1.14 (s, 3H); MS 704 (M+1).

Example 8

N-(4-Azido-2,3,5,6-tetrafluoro-benzyl)gambogamide

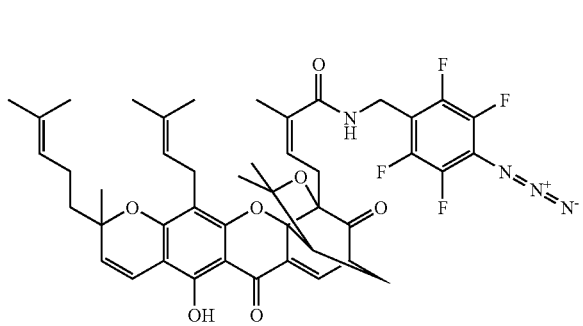

A mixture of gambogic acid (61 mg, 0.097 mmol), DMAP (11.9 mg, 0.097 mmol), EDCI (22.3 mg, 0.12 mmol), triethylamine (0.05 mL) and 4-azido-2,3,5,6-tetrafluoro-benzylamine hydrochloride (25 mg, 0.097 mmol) in dichloromethane (5 mL) was stirred at room temperature for 48 h. The solution was poured into water (10 mL) and extracted with ethyl acetate (3×30 mL). The combined organic layer was dried and concentrated to give crude product, which was purified by chromatography (SiO$_2$, EtOAc/Hexane 1:5) to give 40 mg (49%) of the title compound. $^1$H NMR (CDCl$_3$): 12.82 (s, 1H), 7.54 (d, J=6.90 Hz, 1H), 6.67 (d, J=10.5 Hz, 1H), 5.45 (d, J=10.2 Hz, 1H), 5.31 (t, J=8.7 Hz, 1H), 5.05-4.98 (m, 2H), 4.84-4.39 (m, 2H), 3.45 (s, 1H), 3.56-3.13 (m, 2H), 2.62-2.51 (m, 2H), 2.32-2.20 (m, 2H), 2.10-1.95 (m, 2H), 1.78 (s, 3H), 1.72 (s, 3H), 1.67 (s, 3H), 1.64 (s, 3H), 1.56 (bs, 6H), 1.44 (s, 3H), 1.23 (s, 3H); MS. 831 (M+1).

Example 9

N-(1,2-Dicarboxylethyl)gambogamide

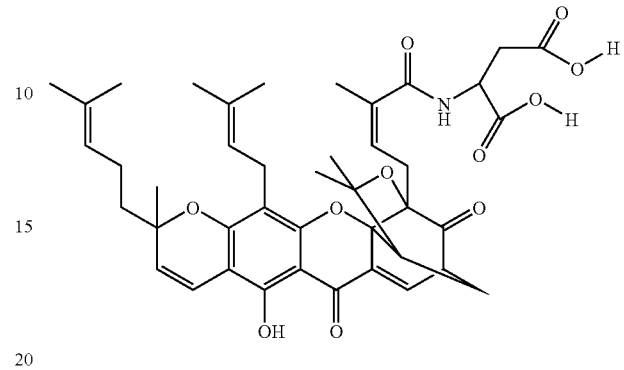

A solution of aspartic acid (133.1 mg, 1 mmol), N-hydroxysuccinimidyl gambogate (362 mg, 0.5 mmol) and triethylamine (0.1 mL) in anhydrous DMSO (10 mL) was stirred for 48 h. It was diluted with water (50 mL) and extracted with ethyl acetate (3×20 mL). The combined organic layer was extracted with saturated aqueous sodium bicarbonate (20 mL). The basic aqueous layer was acidified with 1N HCl to pH=2 and was extracted with ethyl acetate (3×20 mL). The combined organic layer was dried, concentrated to give 110 mg (30%) of the title compound. $^1$H NMR (CDCl$_3$): 12.80 (s) and 12.70 (s) (1H), 7.56-7.54 (m, 1H), 6.67-6.60 (m, 1H), 5.56-5.52 (m, 1H), 5.47-5.43 (m, 1H), 5.22 (t, J=6.0 Hz, 1H), 5.07 (m, 1H), 4.84 (m, 1H), 3.55-3.20 (m, 8H), 3.20-2.30 (m, 5H), 1.76-1.74 (3H), 1.71-1.69 (3H), 1.65 (bs, 6H), 1.56 (s, 3H), 1.43-1.41 (3H), 1.34 (s, 3H), 1.28-1.26 (3H); MS. 744 (M+1).

Example 10

N-(4-Azidobenzohydrazide)gambogamide

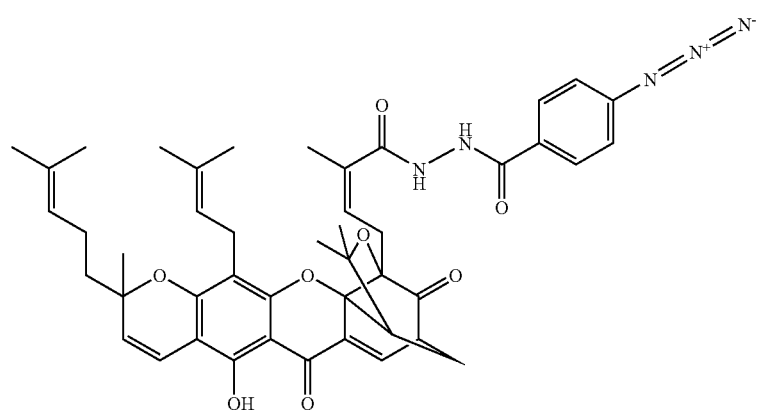

To a solution of gambogic acid (352 mg, 0.56 mmol) and DMAP (68.4 mg, 0.56 mmol) in anhydrous $CH_2Cl_2$ (10 mL) was added 1-(3-dimethylamino-propyl)-3-ethyl-carbodiimide hydrochloride (EDCI) (107.3 mg, 0.56 mmol). The orange solution was stirred at room temperature for 20 min, and 4-azidobenzohydrazide (100 mg, 0.56 mmol) was then added. The reaction mixture was stirred at room temperature for 4 h. It was diluted with ethyl acetate (40 ml) and washed with brine (3×20 mL), dried over $Na_2SO_4$ and concentrated in vacuo, and the residue was purified by repeated preparative TLC (Hexane/EtOAc=3:1) to give 21 mg (5%) of the title compound. $^1H$ NMR ($CDCl_3$) 12.85 (s, 1H), 8.95 (bs, 1H), 8.45 (bs, 1H), 7.85 (d, J=7.8 Hz, 2H), 7.61 (d, J=6.3 Hz, 1H), 7.10 (d, J=7.8 Hz, 2H), 6.66 (d, J=10.3 Hz, 1H), 5.96 (bs, 1H), 5.48 (d, J=10.2 Hz, 1H), 5.30 (m, 1H), 5.06 (m, 1H), 3.55 (t, J=7.2 Hz, 1H), 3.31 (d, J=7.2 Hz, 2H), 2.80-2.55 (m, 3H), 2.55 (d, J=9.3 Hz, 1H), 2.35 (m, 1H), 2.05 (m, 3H), 1.76 (s, 3H), 1.73 (s, 3H), 1.67 (s, 3H), 1.58 (bs, 9H), 1.56 (s, 3H), 1.42 (s, 3H); M.S. 788 (M+1), 810 (M+23).

Example 11

Identification of Derivatives of Gambogic Acid as Antineoplastic Compounds that are Caspase Cascade Activators and Apoptosis Inducers Human breast cancer cell lines T-47D and DLD were grown according to media component mixtures designated by American Type Culture Collection+10% FCS Invitrogen Corporation), in a 5% $CO_2$-95% humidity incubator at 37° C. T-47D and DLD cells were maintained at a cell density between 30 and 80% confluency and for HL-60 at a cell density of 0.1 to 0.6×10$^6$ cells/ml. Cells were harvested at 600×g and resuspended at 0.65×10$^6$ cells/mL into appropriate media+10% FCS. An aliquot of 45 µl of cells was added to a well of a 96-well microtiter plate containing 5 µl of a 10% DMSO in RPMI-1640 media solution containing 1.6 to 100 µM of novel derivative of gambogic acid (0.16 to 10 µM final). An aliquot of 45 µl of cells was added to a well of a 96-well microtiter plate containing 5 µl of a 10%. DMSO in RPMI-1640 media solution without test compound as the control sample. The samples were mixed by agitation and then incubated at 37° C. for 24 h in a 5% $CO_2$-95% humidity incubator. After incubation, the samples were removed from the incubator and 50 µl of a solution containing 20 µM of N-(Ac-DEVD)-N'-ethoxycarbonyl-R110 fluorogenic substrate SEQ ID NO:1 (Cytovia, Inc.; U.S. Pat. No. 6,335,429), 20% sucrose (Sigma), 20 mM DTT (Sigma), 200 mM NaCl (Sigma), 40 mM Na PIPES buffer pH 7.2 (Sigma), and 500 µg/ml lysolecithin (Calbiochem) was added. The samples were mixed by agitation and incubated at room temperature. Using a fluorescent plate reader (Model 1420 Wallac Instruments), an initial reading (T=0) was made approximately 1-2 min after addition of the substrate solution, employing excitation at 485 nm and emission at 530 nm, to determine the background fluorescence of the control sample. After approximately 3 h of incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU_{(T=0)} = \text{Net } RFU_{(T=3h)}$$

The activity of caspase cascade activation was determined by the ratio of the net RFU value for derivatives of gambogic acid to that of control samples. The $EC_{50}$ (nM) was determined by a sigmoidal dose-response calculation (Prism 2.0, GraphPad Software Inc.). The caspase activity (Ratio) and potency ($EC_{50}$) are summarized in Table I:

TABLE I

| | Caspase Activity and Potency | | | |
|---|---|---|---|---|
| | T-47D | | DLD | |
| Example # | Ratio | EC50 (nM) | Ratio | EC50 (nM) |
| 1 | 18 | 303 | 7.6 | 350 |
| 2 | 17 | 676 | 7.2 | 1041 |
| 3 | 13 | 1655 | 5.8 | 2123 |
| 4 | 15 | 638 | 7.2 | 824 |
| 5 | 17 | 750 | 7.2 | 1291 |
| 6 | 17 | 1165 | 9.2 | 2395 |
| 7 | 16 | 1110 | 5.8 | 1358 |

Thus, derivatives of gambogic acid are identified as potent caspase cascade activators and antineoplastic compounds in this assay.

Example 12

Identification of Novel Derivatives of Gambogic Acid as Antineoplastic Compounds that Inhibit Cell Proliferation ($GI_{50}$)

T-47D, DLD-1, MX-1, SW620, H1299, HEK293T and HEK293H cells were grown and harvested as in Example 11. An aliquot of 90 µL of cells (2.2×10$^4$ cells/mL) was added to a well of a 96-well microtiter plate containing 10 µl of a 10% DMSO in RPMI-1640 media solution containing 1 nM to 100 µM of novel derivative of gambogic acid (Example 2; 0.1 nM to 10 µM final). An aliquot of 90 µL of cells was added to a well of a 96-well microtiter plate containing 10 µL of a 10% DMSO in RPMI-1640 media solution without compound as the control sample for maximal cell proliferation ($A_{Max}$). The samples were mixed by agitation and then incubated at 37° C. for 48 h in a 5% $CO_2$-95% humidity incubator. After incubation, the samples were removed from the incubator and 20 µL of CellTiter 96 AQ$_{UEOUS}$ One Solution Cell Proliferation™ reagent (Promega) was added. The samples were mixed by agitation and incubated at 37° C. for 2-4 h in a 5% $CO_2$-95% humidity incubator. Using an absorbance plate reader (Model 1420 Wallac Instruments), an initial reading (T=0) was made approximately 1-2 min after addition of the solution, employing absorbance at 490 nm. This determines the possible background absorbance of the test compounds. No absorbance for the derivative of gambogic acid was found at 490 nm. After the 2-4 h incubation, the samples were read for absorbance as above ($A_{Test}$).

Baseline for $GI_{50}$ (dose for 50% inhibition of cell proliferation) of initial cell numbers were determined by adding an aliquot of 90 µL of cells or 90 µL of media, respectively, to wells of a 96-well microtiter plate containing 10 µL of a 10% DMSO in RPMI-1640 media solution. The samples were mixed by agitation and then incubated at 37° C. for 0.5 h in a 5% $CO_2$-95% humidity incubator. After incubation, the samples were removed from the incubator and 20 uL of CellTiter 96 AQ$_{UEOUS}$ One Solution Cell Proliferation™ reagent (Promega) was added. The samples were mixed by agitation and incubated at 37° C. for 2-4 h in a 5% $CO_2$-95% humidity incubator. Absorbance was read as above, ($A_{Start}$) defining absorbance for initial cell number used as baseline in $GI_{50}$ determinations.

Calculation:

GI$_{50}$ (dose for 50% inhibition of cell proliferation) is the concentration where $[(A_{Test}-A_{Start})/(A_{Max}-A_{Start})]=0.5$.

The GI$_{50}$ (nM) are summarized in Table II:

TABLE II

GI$_{50}$ in Cancer Cells

| Cancer cells | GI$_{50}$ (nM) Example 2 |
| --- | --- |
| T47D | 187 |
| DLD | 173 |
| MX-1 | 101 |
| SW620 | 180 |
| H1299 | 184 |
| HEK293T | 440 |
| HEK293H | 192 |

Thus, novel derivative of gambogic acid (Example 2) is identified as antineoplastic compound that inhibits cell proliferation in several cancer cell lines.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound selected from the group consisting of:
2-(Morpholin-4-yl)-ethyl gambogate;
2-Dimethylaminoethyl gambogate;
N-[3-(4-Methyl-piperazin-1-yl)-propyl]gambogamide;
N-(3-Morpholin-4-yl-propyl)gambogamide;
Methyl 37,38-Dihydroxy-gambogate;
Methyl 37,38-Dihydroxy-9,10-dihydro-10-morpholinyl-gambogate;
Methyl 20-Ethylaldehyde-9,10-dihydro-10-morpholinyl-morellinate;
N-(4-Azido-2,3,5,6-tetrafluoro-benzyl)gambogamide;
N-(1,2-Dicarboxylethyl)gambogamide; and
N-(4-Azidobenzohydrazide)gambogamide.

2. The compound of claim 1 selected from the group consisting of:
2-(Morpholin-4-yl)-ethyl gambogate;
2-Dimethylaminoethyl gambogate;
N-[3-(4-Methyl-piperazin-1-yl)-propyl]gambogamide;
N-(3-Morpholin-4-yl-propyl)gambogamide;
Methyl 37,38-Dihydroxy-gambogate;
Methyl 37,38-Dihydroxy-9,10-dihydro-10-morpholinyl-gambogate; and
Methyl 20-Ethylaldehyde-9,10-dihydro-10-morpholinyl-morellinate.

3. A pharmaceutical composition, comprising a compound of claim 1 and a pharmaceutically acceptable carrier.

4. The pharmaceutical composition of claim 3, wherein said compound is administered together with at least one compound selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, ocreotide, retinoic acid, tamoxifen, Herceptin®, Rituxan®, arsenic trioxide, gemcitabine, doxazocin, terazosin, tamsulosin, CB-64D, CB-184, haloperidol, lovastatin, simvastatin, pravastatin, fluvastatin, atorvastatin, cerivastatin, amprenavir, abacavir, CGP-73547, CGP-61755, DMP-450, indinavir, nelfinavir, tipranavir, ritonavir, saquinavir, ABT-378, AG 1776, BMS-232,632, bexarotene, tretinoin, 13-cis-retinoic acid, 9-cis-retinoic acid, α-difluoromethylomithine, 1LX23-7553, fenretinide, N-4-carboxyphenyl retinamide, lactacystin, MG-132, PS-341, Gleevec®, ZD1839 (Iressa), SH268, genistein, CEP2563, SU6668, SU11248, EMD121974, R115777, SCH66336, L-778,123, BAL9611, TAN-1813, flavopiridol, UCN-01, roscovitine, olomoucine, celecoxib, valdecoxib, rofecoxib and alanosine.

* * * * *